| United States Patent [19]
Hughes et al.

[11] Patent Number: 4,748,266
[45] Date of Patent: May 31, 1988

[54] SUBSTITUTED 2-OXOCYCLOHEXANEACETIC ACID ESTERS

[75] Inventors: Philip F. Hughes, Hopewell; Dominick Mobilio, Plainsboro; Leslie G. Humber, North Brunswick, all of N.J.

[73] Assignee: American Home Products Corporation, New York, N.Y.

[21] Appl. No.: 20,426

[22] Filed: Mar. 2, 1987

Related U.S. Application Data

[63] Continuation-in-part of Ser. No. 868,230, May 28, 1986, abandoned.

[51] Int. Cl.$^4$ .................... C07C 69/74; C07C 69/76
[52] U.S. Cl. .................................. 560/51; 560/118; 560/125
[58] Field of Search .................... 560/51, 118, 125

[56] References Cited

U.S. PATENT DOCUMENTS 3,435,063  3/1969  Machleidt et al. ............. 560/125 X
4,616,028  10/1986  Mobilio et al. ..................... 514/411

FOREIGN PATENT DOCUMENTS 43-12584  5/1968  Japan .................................. 560/122
0108838   8/1980  Japan .................................. 560/125

OTHER PUBLICATIONS

A. A. Asselin et al, J. Med. Chem. 19(6) 787–791 (1976).
A. A. Asselin et al, J. Med. Chem. 19(6) 792–797 (1976).

Primary Examiner—Donald B. Moyer
Assistant Examiner—Patricia M. Scott
Attorney, Agent, or Firm—Walter Patton

[57] ABSTRACT

Process for the production of substituted 2-oxocyclohexaneacetic acid esters and intermediates used for their production. The substituted 2-oxocyclohexaneacetic acid esters are themselves useful intermediates for the manufacture of substituted 2,3,4,9-tetrahydro-1H-carbazole-1-acetic acid derivatives having useful analgesic and anti-inflammatory activity.

3 Claims, No Drawings

SUBSTITUTED 2-OXOCYCLOHEXANEACETIC ACID ESTERS

This is a continuation-in-part application of copending United States patent application, U.S. Ser. No. 868,230, filed May 28, 1986, now abandoned.

BACKGROUND OF THE INVENTION a. Field of Invention

This invention relates to the process for the production of substituted 2-oxocyclohexaneacetic acid esters and the intermediates used for their production. The substituted 2-oxocyclohexaneacetic acid esters produced by the present process are themselves intermediates for the manufacture of useful analgesic and anti-inflammatory compounds described in Mobilio et al, U.S. Pat. No. 4,616,028, Oct. 7, 1986, which is herein incorporated by reference.

More specifically, this invention relates to the production of 1,4-disubstituted 2-oxocyclohexaneacetic acid esters of formula (V)

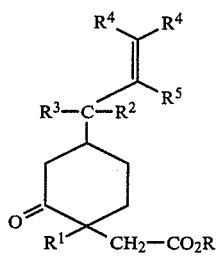

(V)

wherein R and $R^1$ are lower alkyl; $R^2$, $R^3$, and $R^5$ are hydrogen, or lower alkyl wherein lower alkyl contains 1 to 6 carbon atoms; each $R^4$ is independently selected from the group consisting of hydrogen, or lower alkyl wherein lower alkyl contains 1 to 6 carbon atoms, or $R^3$ is joined to the $R^4$ which is cis to the carbon bearing $R^3$ to form $-(CH_2)_m$ wherein m is 2 to 3, or $R^5$ is joined to the $R^4$ which is cis to $R^5$ to form $-CH=CH-CH=CH-$.

b. Prior Art

The closest prior art to the present invention is:

Mobilio et al, U.S. Pat. No. 4,616,028. Mobilio et al disclose the 1,4-disubstituted 2-oxocyclohexaneacetic acid esters of formula (V) and the process for producing analgesic and anti-inflammatory compounds from said 2-oxocyclohexaneacetic acid esters of formula (V). Mobilio et al employ the expensive phenylseleneyl chloride in the production process of the 2-oxocyclohexaneacetic acid esters of formula (V). The present invention provides a novel process for producing said 2-oxocyclohexaneacetic acid esters in high yield, from inexpensive reagents which can be conveniently carried out on a large scale without the necessity for purifying intermediate compounds by chromatography. The present process also provides a high yield of the preferred isomer of 2-oxocyclohexaneacetic acid esters of formula (V).

A. Asselin et al, J. Med. Chem., 19, 787 (1976) disclose an alternate production method for a substituted 2-oxocyclohexaneacetic acid esters of formula (V).

A. Asselin et al, U.S. Pat. No. 4,057,559, Nov. 8, 1977, disclose still another process for the production of a substituted 2-oxocyclohexaneacetic acid esters of formula (V).

SUMMARY OF THE INVENTION

The novel intermediate compounds of this invention are represented by formulas (IV), (III) and (II):

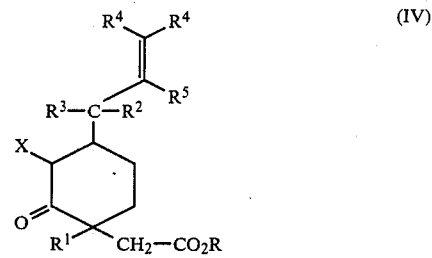

wherein R and $R^1$ are lower alkyl; $R^2$, $R^3$, and $R^5$ are hydrogen, or lower alkyl wherein lower alkyl contains 1 to 6 carbon atoms; each $R^4$ is independently selected from the group consisting of hydrogen, or lower alkyl wherein lower alkyl contains 1 to 6 carbon atoms, or $R^3$ is joined to the $R^4$ which is cis to the carbon bearing $R^3$ to form $-(CH_2)_m$ wherein m is 2 to 3, or $R^5$ is joined to the $R^4$ which is cis to $R^5$ to form $-CH=CH-CH=CH-$; and X is chlorine, or bromine;

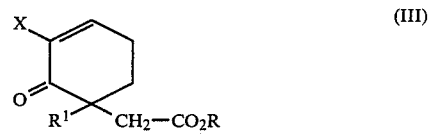

wherein R and $R^1$ are lower alkyl wherein lower alkyl contains 1 to 6 carbon atoms; X is bromine, or chlorine; and

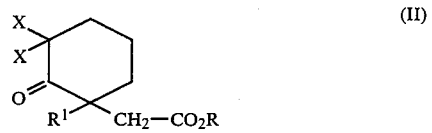

wherein R and $R^1$ are lower alkyl wherein lower alkyl contains 1 to 6 carbon atoms; and X is chlorine, or bromine.

Included in the present invention are the diastereoisomers of formula (IV) wherein the 4-substituent is either cis or trans to the acetic acid chain at position one. Racemic mixtures of such compounds are herein designated (IV-(±)cis) and (IV-(±)trans).

Also included in this invention are the optical isomers of the compounds of formula (IV) which result from asymmetric centers, contained therein. Such isomers are obtained in substantially pure form by classical separation techniques and by sterically controlled synthesis.

The preferred intermediate compounds of the present invention are the isomers of the 2-oxocyclohexaneacetic acid esters represented by formulas (IVa-(±)cis) and (IVb-(±)cis):

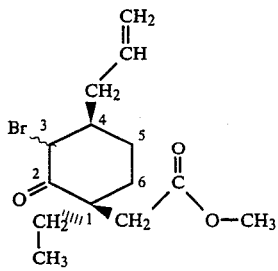
(IVa-(±)cis)

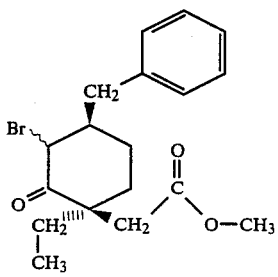
(IVb-(±)cis)

wherein the 1-acetic acid methyl ester group is cis to the 4-(2-propenyl) group, or the 4-(phenylmethyl) group.

The novel process for the production of the known intermediate compounds of formula (V)

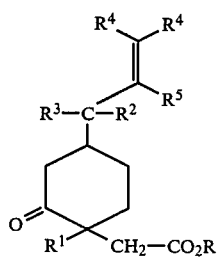
(V)

wherein R and R¹ are lower alkyl; R², R³, and R⁵ are hydrogen, or lower alkyl wherein lower alkyl contains 1 to 6 carbon atoms; each R⁴ is independently selected from the group consisting of hydrogen, or lower alkyl wherein lower alkyl contains 1 to 6 carbon atoms, or R³ is joined to the R⁴ which is cis to the carbon bearing R³ to form $-(CH_2)_{\overline{m}}$ wherein m is 2 to 3, comprises (a) dihalogenating the compound of formula (I)

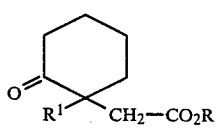
(I)

[compound (I) is obtained by the process of A. Asselin et al, J. Med. Chem., 19, 787 (1976)] wherein R and R¹ are as defined above with a halogenating agent such as bromine, cupric bromide, or sulfuryl chloride in a suitable solvent such as methylene chloride, chloroform, methanol, diethyl ether, or acetic acid to produce the novel intermediate compound (II)

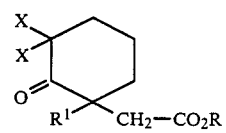
(II)

wherein R, R¹, and X are as defined above;

(b) dehydrohalogenating compound (II) in the presence of a base such as lithium carbonate, calcium carbonate, diazabicycloundecane, or collidine with or without added salts such as lithium bromide, or sodium chloride in a suitable solvent such as N,N-dimethylformamide, or dimethylsulfoxide to produce the novel intermediate compound (III)

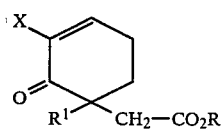
(III)

wherein R, R¹, and X are as defined above;

(c) reacting the compound (III) with

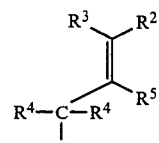

wherein R², and R³, and R⁵ are hydrogen, or lower alkyl wherein lower alkyl contains 1 to 6 carbon atoms; each R⁴ is independently selected from the group consisting of hydrogen, or lower alkyl wherein lower alkyl contains 1 to 6 carbon atoms, or R³ is joined to one of the R⁴ substituents to form $-(CH_2)_{\overline{m}}$ wherein m is 2 to 3; and Y is SiR⁶R⁷R⁸, of SnR⁶R⁷R⁸ wherein R⁶, R⁷, and R⁸ are independently selected from the group consisting of hydrogen, straight chain or branched lower alkyl containing 1 to 6 carbon atoms, cycloalkyl, aryl, arylalkyl, halogen, or alkoxy, werein the reaction is carried out in the presence of a Lewis acid such as titanium tetrachloride, tin (IV) chloride, zinc chloride, zinc bromide, magnesium chloride, or magnesium bromide, as described in H. Sakurai, Pure & Appl. Chem., 54, 1 (1982) and D. Seyferth et al, J. Org. Chem., 26, 4797 (1961) to produce the novel intermediate compound (IV)

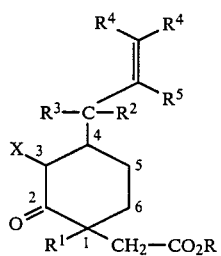
(IV)

wherein R and R¹ are lower alkyl; R², R³, and R⁵ are hydrogen, or lower alkyl wherein lower alkyl contains 1 to 6 carbon atoms; each R⁴ is independently selected from the group consisting of hydrogen, or lower alkyl wherein lower alkyl contains 1 to 6 carbon atoms, or $R^3$ is joined to the $R^4$ which is cis to the carbon bearing $R^3$ to form $-(CH_2)_{\overline{m}}$ wherein m is 2 to 3; X is chlorine, or bromine wherein the isomer where the group at position 4 is cis to the acetic acid ester group at position 1 predominates over the trans isomer;

(d) dehalogenating the compound (IV) with a reducing agent such as zinc in a weak acid, or with sodium dithionite to produce the desired known compound (V).

The novel process for the production of the known intermediate compounds of formula (V)

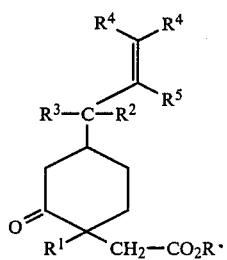
(V)

wherein R and $R^1$ are lower alkyl; $R^2$ and $R^3$ are hydrogen, or lower alkyl wherein lower alkyl contains 1 to 6 carbon atoms; the $R^4$ which is trans to $R^5$ is selected from the group consisting of hydrogen, or lower alkyl wherein lower alkyl contains 1 to 6 carbon atoms, and $R^5$ is joined to the $R^4$ which is cis to $R^5$ to form $-CH=CH-CH=CH-$ comprises (a) reacting the compound (III) with

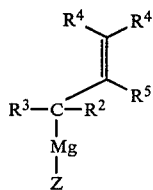
(VI)

wherein $R^2$ and $R^3$ are hydrogen, or lower alkyl wherein lower alkyl contains 1 to 6 carbon atoms; the $R^4$ which is trans to $R^5$ is selected from the group consisting of hydrogen, or lower alkyl wherein lower alkyl contains 1 to 6 carbon atoms, and $R^5$ is joined to the $R^4$ which is cis to $R^5$ to form $-CH=CH-CH=CH-$; Z is Cl, Br, or I, in the presence of a copper salt such as copper (I) bromide-dimethyl sulfide complex, cuprous iodide, cuprous bromide, copper acetate, cuprous chloride, tributylphosphine cuprous iodide complex, or cuprous cyanide, and simultaneously in the presence of a Lewis acid such as titanium tetrachloride, zinc bromide, zinc iodide, zinc triflate, lithium bromide, lithium iodide, magnesium bromide, magnesium chloride, magnesium triflate, or stannic chloride. A preferred method involves adding (VI) (Z=Br) to (III) in the presence of about 0.1 molar equivalents of copper (I) bromide-dimethyl sulfide complex and about 1 molar equivalent of zinc bromide to produce the novel intermediate compound (IV)

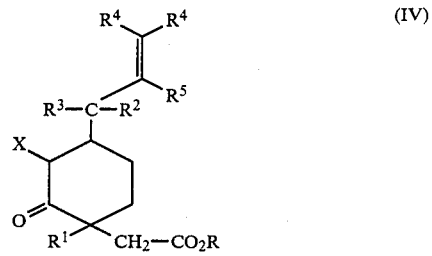

wherein R and $R^1$ are lower alkyl; $R^2$ and $R^3$ are hydrogen, or lower alkyl wherein lower alkyl contains 1 to 6 carbon atoms; the $R^4$ which is trans to $R^5$ is selected from the group consisting of hydrogen, or lower alkyl wherein lower alkyl contains 1 to 6 carbon atoms, and $R^5$ is joined to the $R^4$ which is cis to $R^5$ to form $-CH=CH-CH=CH-$; and X is chlorine or bromine wherein the isomer where the group at position 4 is cis to the acetic acid ester group at position 1 predominates over the trans isomer;

(b) dehalogenating the compound (IV9 with a reducing agent such as zinc in a weak acid, or with sodium dithionite to produce the desired known compound (V).

The following examples further illustrate this invention.

EXAMPLE 1

Preparation of
3-Bromo-1-ethyl-2-oxocyclohex-3-eneacetic Acid Methyl Ester (III: R=—CH$_3$; R$^1$=—C$_2$H$_5$; X=—Br)

A 5% (v/v) solution of bromine in methylene chloride (136 mL, 127 mmol, 2.5 eq) was added dropwise to a stirred solution of 1-ethyl-2-oxocyclohexaneacetic acid methyl ester (10.0 g, 50.5 mmol) prepared by the process of A. Asselin et al. J. Med. Chem., 19, 787 (1976). The mixture was stirred an additional thirty minutes and treated with isobutylene to consume the excess bromine. The reaction mixture was concentrated to give 20.2 g (>100%) of 3,3-dibromo-1-ethyl-2-oxocyclohexaneacetic acid methyl ester as an orange oil (a portion of the oil was recrystallized from hexanes to give a solid m.p. 61°–62° C.). The oil was dissolved in N,N-dimethylformamide (62 mL) and treated with lithium bromide (6.4 g, 74 mmol) and lithium carbonate (3.9 g, 54 mmol). The reaction mixture was heated with stirring to 100° C. for one hour. The reaction mixture was poured into water (100 mL) and extracted with toluene (4×100 mL). The toluene extracts were washed with water (4×50 mL), dried (MgSO$_4$) and concentrated to give 13.8 g (99%) of 3-bromo-1-ethyl-2-oxocyclohex-3-eneacetic acid methyl ester as a light orange oil. This product was used in Example 2 without further purification.

NMR (CDCl$_3$, 200 MHz) δ 0.87 (3H, t), 1.65 (2H, dq), 2.3–2.6 (5H, m), 2.9 (1H, d), 3.65 (3H, s), 7.3 (1H, m).

EXAMPLE 2

Preparation of
3-Bromo-1-ethyl-2-oxo-4-(2-propenyl)cyclohexaneacetic Acid Methyl Ester (IV: R=—CH$_3$; R$^1$=—C$_2$H$_5$; R$^2$, R$^3$, R$^4$, R$^5$=—H; X=—Br)

3-Bromo-1-ethyl-2-oxocyclohex-3-eneacetic acid methyl ester (13.8 g, 50.2 mmol) was dissolved in CH$_2$Cl$_2$ (distilled from CaH, 50 mL) and cooled to −20° C. The mixture was treated dropwise with TiCl$_4$ (14.28 g, 75.3 mmol) followed after one hour by allyltrimethylsilane (6.9 g, 9.6 mL, 60.2 mmol). The mixture was stirred for one hour at −20° C. then quenched with methanol (42 mL) followed by water (56 mL). The mixture was then extracted with toluene (4×150 mL). The combined toluene extracts were washed with saturated sodium chloride solution (100 mL), dried (MgSO$_4$), and concentrated to give 15.9 g (99%) of an isomeric mixture of 3-bromo-1-ethyl-2-oxo-4-(2-propenyl)cyclohexaneacetic acid methyl ester. This product was used in Example 3 without further purification.

NMR (CDCl$_3$, 200 MHz) δ 0.8 (3H, t), 1.5–2.8 (11H, m), 3.6 (3H, s), 5.0–5.2 (3H, m), 5.5–5.8 (1H, m).

This compound crystallized on prolonged standing.

EXAMPLE 3

Preparation of
cis-1-Ethyl-2-oxo-4-(2-propenyl)cyclohexaneacetic
Acid Methyl Ester (Va-(±)cis)

3-Bromo-1-ethyl-2-oxo-4-(2-propenyl)cyclohexaneacetic acid methyl ester (15.9 g, 50.3 mmol) was dissolved in acetic acid (107 mL) and treated with zinc dust (19.4 g, 302 mmol). The stirred mixture was heated to 100° C. for five hours then cooled to room temperature. The excess zinc was filtered off and washed with water (50 mL) and toluene (50 mL). The filtrate was then added to more water (100 mL) and extracted with toluene (3×150 mL). The combined toluene estracts were then washed with a saturated sodium bicarbonate solution, dried (MgSO$_4$) and concentrated to give 11.14 g (93%) of cis-1-ethyl-2-oxo-4-(2-propenyl)cyclohexaneacetic acid methyl ester as a yellowish oil. The oil was distilled (108°–113° C. at 0.3 mmHg) to give 10.06 g (84%) of the product as a clear oil.

Gas chromatography analysis showed a 7.5:1 cis:trans isomer ratio.

NMR (CDCl$_3$, 200 MHz) δ 0.8 (3H, t), 1.5–2.6 (13H, m), 3.6 (3H, s), 5.0–5.1 (2H, m), 5.6–5.8 (1H, m).

The isomer ratio (cis:trans), after bromine removal in Example 3, was 7.5:1. Subsequent experiments indicated that better selectivity (isomer ratio 15:1) was obtained in Example 3 by adding the allyltrimethylsilane dropwise as a 20% methylene chloride solution over an hour in Example 2.

EXAMPLE 4

Preparation of
cis-1-Ethyl-2-oxo-4-(2-propenyl)cyclohexaneacetic
Acid Methyl Ester (Va-(±)cis)

3-Bromo-1-ethyl-2-oxo-4-(2-propenyl)cyclohexaneacetic acid methyl ester (200 mg, 0.631 mmol) and sodium dithionite (1.1 g, 6.31 mmol) were dissolved in N,N-dimethylformamide:water (5 mL each) and stirred under N$_2$ for two days. The solvents were then removed under vacuum (0.1 mmHg) at room temperature. The residue was partitioned between ether (100 mL) and water (50 mL). The ether layer was dried (MgSO$_4$) and concentrated to give a slightly yellow oil. The product was then purified by bulb-to-bulb distillation (85° C. at 0.1 mmHg) to give 128 mg (85%) of cis-1-ethyl-2-oxo-4-(2-propenyl)cyclohexaneacetic acid methyl ester, identical by NMR to the product of Example 3.

EXAMPLE 5

Preparation of
cis-1-Ethyl-2-oxo-4-(phenylmethyl)cyclohexaneacetic
Acid Methyl Ester (Vb-(±)cis)

A solution of 3-bromo-1-ethyl-2-oxocyclohex-3-eneacetic acid methyl ester (10 g, 36.3 mmol, as prepared in Example 1) and copper (I) bromide-dimethyl sulfide complex (3.63 mmol, 746 mg) in 107 mL of dry tetrahydrofuran was stirred at 0° C. under nitrogen and treated with anhydrous zinc bromide (36.6 mmol, 8.17 g). After 5 minutes, the mixture was treated dropwise with 36.6 mmol of benzylmagnesium chloride (18.2 mL of 2M in THF). After 45 minutes, another 8 mmol of benzylmagnesium chloride were added followed by 350 mg of copper (I) bromide-dimethyl sulfide complex and then another 16 mmol of benzylmagnesium chloride. The reaction was quenched with 150 mL of 1M HCl and extracted with 4×50 ML of ether. The extracts were combined, dried over magnesium sulfate, and concentrated affording 3-bromo-1-ethyl-2-oxo-4-(phenylmethyl)cyclohexaneacetic acid methyl ester. This was then stirred in a solution of 74 mL of N,N-dimethylformamide and 35 mL of water and treated with 109 mmol (18.96 g) of sodium dithionite. The mixture was heated at 55° C. under nitrogen for 20 minutes, poured into 200 mL of water and extracted with 4×100 mL of 1:1 ether-petroleum ether. The extracts were combined, washed with 100 mL of water and 100 mL of saturated sodium bicarbonate (aq), dired over magnesium sulfate, and concentrated affording 10.48 g (36.6 mmol, 100% crude yield) of product as a pale yellow oil. Analysis by capillary GC demonstrated a 4.41:1 ratio of diastereomers, with the cis isomer predominating. The reduction of the intermediate 3-bromo-1-ethyl-2-oxo-4-(phenylmethyl)-cyclohexaneacetic acid methyl ester to the title compound can also be carried out as described in Example 3.

NMR (CDCl$_3$/TMS, 200 MHz) δ 0.8 (t, 3H, J=7.5 Hz), 1.4–2.9 (m, 13H), 3.6 and 3.7 (2s, 3H, OCH$_3$ from major and minor isomers), 7.1–7.5 (m, 5H).

The ketones of Examles 3, 4 or 5 can be subjected to Fischer indole synthesis conditions, as described in Mobilio et al, U.S. Pat. No. 4,616,028, by refluxing with 2-ethylphenylhydrazine or phenylhydrazine in methanol the appropriate time to form the corresponding hydrazone. The hydrazone solution can then be cooled to 0° C., treated with acetyl chloride to generate HCl and refluxed an additional 45 minutes to affect Fischer indole cyclization. The resulting esters can then be hydrolyzed with potassium carbonate in aqueous methanol to afford known substituted tetrahydro-1H-carbazole-1-acetic acids having analgesic and anti-inflammatory activity.

The demonstration of analgesic and anti-inflammatory activity and the method of treatment of inflammatory or painful conditions is also described in Mobilio et al, U.S. Pat. No. 4,616,028.

We claim:
1. A compound of formula (IV)

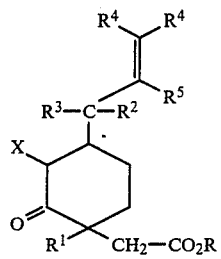
(IV)

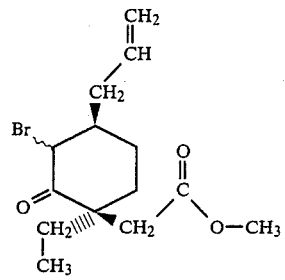
(IVa-(±)cis)

wherein R and $R^1$ are lower alkyl; $R^2$, $R^3$, and $R^5$ are hydrogen, or lower alkyl wherein lower alkyl contains 1 to 6 carbon atoms; each $R^4$ is independently selected from the group consisting of hydrogen, or lower alkyl wherein lower alkyl contains 1 to 6 carbon atoms, or $R^3$ is joined to the $R^4$ which is cis to the carbon bearing $R^3$ to form $-(CH_2)_m-$ wherein m is 2 to 3, or $R^5$ is joined to the $R^4$ which is cis to $R^5$ to form $-CH=CH-CH=CH-$; and X is chlorine, or bromine.

2. The compound of formula (IVa-(±)cis) according to claim 1.

3. The compound of formula (IVb-(±)cis)

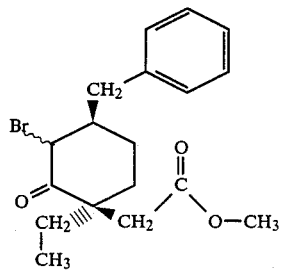
(IVb-(±)cis)

according to claim 1.

* * * * *